(12) United States Patent
Hu

(10) Patent No.: US 10,683,264 B2
(45) Date of Patent: Jun. 16, 2020

(54) PROCESS FOR PRODUCING TAURINE

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 16/201,524

(22) Filed: Nov. 27, 2018

(65) Prior Publication Data

US 2019/0135739 A1    May 9, 2019

Related U.S. Application Data

(63) Continuation-in-part of application No. 15/894,382, filed on Feb. 12, 2018, now abandoned, which is a continuation-in-part of application No. 15/832,667, filed on Dec. 5, 2017, now Pat. No. 10,112,894, which is a continuation-in-part of application No. 15/495,297, filed on Apr. 24, 2017, now Pat. No. 9,926,265, which is a continuation-in-part of application No. 15/366,798, filed on Dec. 1, 2016, now Pat. No. 9,815,778, which is a continuation-in-part of application No. 15/268,071, filed on Sep. 16, 2016, now Pat. No. 9,745,258.

(51) Int. Cl.
    *C07C 303/02* (2006.01)
    *C07C 303/44* (2006.01)
    *C07C 303/32* (2006.01)
    *C07C 309/14* (2006.01)

(52) U.S. Cl.
    CPC .......... *C07C 303/02* (2013.01); *C07C 303/32* (2013.01); *C07C 303/44* (2013.01); *C07C 309/14* (2013.01)

(58) Field of Classification Search
    CPC ... C07C 303/02; C07C 303/32; C07C 303/44; C07C 309/14
    See application file for complete search history.

(56) References Cited

U.S. PATENT DOCUMENTS

| | | |
|---|---|---|
| 1,932,907 A | 10/1933 | Nicodemus, et al. |
| 1,999,614 A | 4/1935 | Nicodemus, et al. |
| 2,109,401 A | 2/1938 | Nicodemus |
| 2,510,281 A | 6/1950 | Gold |
| 2,693,488 A | 11/1954 | Sexton |
| 2,820,818 A | 1/1958 | Sexton et al. |
| 3,326,895 A | 6/1967 | Coker |
| 4,444,694 A * | 4/1984 | Hsieh .................... C07C 309/14 562/104 |
| 4,657,704 A * | 4/1987 | Yamamoto ............ C07C 303/02 562/104 |
| 5,646,320 A | 7/1997 | Cassady et al. |
| 5,739,365 A | 4/1998 | Briody et al. |
| 8,609,890 B1 | 12/2013 | Hu |
| 9,061,976 B1 | 6/2015 | Hu |
| 9,108,907 B1 | 8/2015 | Hu |
| 9,428,450 B2 | 8/2016 | Hu |
| 9,428,451 B2 | 8/2016 | Hu |
| 9,573,890 B2 | 2/2017 | Hu |
| 9,593,076 B2 | 3/2017 | Hu |
| 9,598,357 B1 * | 3/2017 | Hu .................... C07C 303/22 |
| 9,598,360 B2 | 3/2017 | Hu |
| 9,745,258 B1 | 8/2017 | Hu |
| 9,815,778 B1 | 11/2017 | Hu |
| 9,850,200 B1 | 12/2017 | Hu |
| 9,926,265 B1 | 3/2018 | Hu |
| 9,994,517 B1 | 6/2018 | Hu |
| 10,040,755 B2 | 8/2018 | Hu |
| 10,071,955 B1 | 9/2018 | Chen et al. |
| 10,112,894 B2 | 10/2018 | Hu |
| 2014/0121405 A1 | 5/2014 | Chen |
| 2015/0299113 A1 | 10/2015 | Hu |
| 2015/0299114 A1 | 10/2015 | Hu |
| 2016/0340300 A1 | 11/2016 | Hu |
| 2016/0355470 A1 | 12/2016 | Hu |
| 2018/0093946 A1 | 4/2018 | Hu |
| 2018/0208553 A1 | 7/2018 | Chen et al. |

FOREIGN PATENT DOCUMENTS

| | | |
|---|---|---|
| CN | 101486669 A | 7/2009 |
| CN | 101508657 A | 8/2009 |
| CN | 101508658 A | 8/2009 |
| CN | 101508659 A | 8/2009 |
| CN | 101717353 A | 6/2010 |
| CN | 102285905 A | 12/2011 |
| CN | 103613517 A | 3/2014 |
| CN | 104945289 A | 9/2015 |

(Continued)

OTHER PUBLICATIONS

U.S. Appl. No. 15/268,071 USPTO Non-Final Office Action, dated Mar. 23, 2017.
U.S. Appl. No. 15/268,071 USPTO Final Office Action, dated Jun. 9, 2017.
U.S. Appl. No. 15/366,798 USPTO Non-Final Office Action, dated Aug. 22, 2017.
CA Application No. 2,977,184 First Office Action, dated Oct. 3, 2017.
CA Application No. 2,977184 Notice of Allowance, dated Nov. 20, 2017.
JP Application No. 2017-159725 Notice of Reasons for Rejection, dated Dec. 5, 2017.
JP Application No. 2017-159725 Decision to Grant, dated Jan. 31, 2018.
EP Application No. 17 187 912.5-1109 Communication under Rule 71(3) EPC Intention to Grant, dated Jun. 14, 2018.

(Continued)

*Primary Examiner* — Yate' K Cutliff
(74) *Attorney, Agent, or Firm* — Myers Wolin, LLC

(57) ABSTRACT

There is disclosed a process for producing taurine by reacting 2-oxazolidinone with ammonium sulfite, or ammonium bisulfite, or a mixture of ammonium sulfite and ammonium bisulfite in an aqueous solution to form ammonium taurinate and ammonium bicarbonate. Taurine is obtained by decomposing ammonium taurinate to taurine and ammonia and recovered by solid-liquid separation.

9 Claims, 3 Drawing Sheets

(56) References Cited

FOREIGN PATENT DOCUMENTS

| CN | 105693559 A | 6/2016 |
|---|---|---|
| CN | 105732440 A | 7/2016 |
| CN | 106008280 A | 10/2016 |
| CN | 106588704 A | 4/2017 |
| CN | 107056659 A | 8/2017 |
| CN | 108329239 A | 7/2018 |
| DE | 219023 A3 | 2/1985 |
| EP | 3284737 A1 | 2/2018 |
| JP | 102094 | 4/1933 |
| JP | S63243066 A | 10/1988 |
| JP | H04352760 A | 12/1992 |
| JP | H08268995 A | 10/1996 |
| JP | 6227815 B1 | 11/2017 |
| JP | 2017206495 A | 11/2017 |
| JP | 2017533883 A | 11/2017 |
| WO | WO 0177071 A1 | 10/2001 |

OTHER PUBLICATIONS

U.S. Appl. No. 15/495,297 USPTO Non-Final Office Action, dated Dec. 12, 2017.
U.S. Appl. No. 15/832,667 USPTO Non-Final Office Action, dated May 14, 2018.
EP Application No. 17187912.5 Extended European Search Report including European search opinion, dated Feb. 3, 2018.
Liu Fuming, Xie Liming, Study on the Ammonolysis Reaction for Taurine, Shandong Chemical Industry, May 2015, 44(5), pp. 27-28,30. (Original in Chinese, English Translation provided).
Liu Fuming, Process Design of the Ammonolysis Reaction of Taurine, China Chemical Trade, Aug. 2013, No. 8, pp. 120. (Original in Chinese; English Translation provided).
Chen, W.R.; Lu, J.P.;Wen, J.H.;Wang, J.F., "The Process of Preparation of Taurine from Ethylenimine,", Zhejiang Chemical Industry, 2011, vol. 42, No. 5, pp. 5, 18-20.
Search Report for Indian Patent Application No. 201917011410 dated Jan. 8, 2020, 2 pages.
Steuerle, U. et al., Aziridines, 2012, Ullmann's Encyclopedia of Industrial Chemistry, vol. 4, pp. 515-522 (Year: 2012).
Bondabera et al., Pharmaceutical Chemistry Journal, Synthesis of Taurine, Mar. 2008, pp. 142-144, vol. 42, No. 3, Springer Science+ Business Media, Inc, Secaucus, New Jersey.
Canadian First Office Action, dated Nov. 2, 2017 for corresponding Canada Application No. 2,946,181.
Curriculum Vitae (CV) of Robert E. Maleczka, dated Jul. 12, 2019, 39 pages, Vitaworks Exhibit 2008.
Database Caplus Chemical Abstracts Service, Columbus, Ohio, U.S.; Database Accession No. 1986:34336, Abstract of DD 219023 Bach et al., Feb. 20, 1985.
Decision re Institution of Inter Partes Review issued for Case IPR2018-01766 for corresponding U.S. Appl. No. 9,428,450, dated Apr. 9, 2019, 45 pages.
Decision re Institution of Inter Partes Review issued for Case IPR2018-01767 for corresponding U.S. Pat. No. 9,428,451, dated Apr. 10, 2019, 25 pages.
Decision re Institution of Inter Partes Review issued for Case IPR2018-01768 for corresponding U.S. Pat. No. 9,573,890, dated Apr. 10, 2019, 23 pages.
Declaration of Mark A. Lipton in Support of Petition for Inter Partes Review of U.S. Pat. No. 9,428,450 Under 37 C.F.R. § 42100, Sep. 28, 2018, pp. 65.
Declaration of Mark A. Lipton in Support of Petition for Inter Partes Review of U.S. Pat. No. 9,428,451 Under 37 C.F.R. § 42100, Sep. 28, 2018, pp. 69.
Declaration of Mark A. Lipton in Support of Petition for Inter Partes Review of U.S. Pat. No. 9,573,890 Under 37 C.F.R. § 42.100, Sep. 28, 2018, pp. 66.
Extended European Search Report and the European Search Opinion completed Apr. 5, 2017 for corresponding European Application No. 17157022.9.
Extended European Search Report issued by the European Patent Office for corresponding European Patent Application No. EP18154790. 2, dated Jun. 25, 2018.
Hubei Grans Life Science and Technology Co., Ltd v. Vitaworks IP, LLC, Case No. IPR2018-01766, Petition for Inter Parte Review of U.S. Pat. No. 9,428,450 Under 37 C.F.R. § 42.100, Sep. 28, 2018, pp. 30, Alexandria, Virginia.
Hubei Grans Life Science and Technology Co., Ltd v. Vitaworks IP, LLC, Case No. IPR2018-01767, Petition for Inter Parte Review of U.S. Pat. No. 9,428,451 Under 37 C.F.R. § 42.100, Sep. 28, 2018, pp. 38, Alexandria, Virginia.
Hubei Grans Life Science and Technology Co., Ltd v. Vitaworks IP, LLC, Case No. IPR2018-01768 Petition for Inter Parte Review of U.S. Pat. No. 9,573,890 Under 37 C.F.R. § 42.100, Sep. 28, 2018, pp. 32, Alexandria, Virginia.
International Search Report and Written Opinion for corresponding International Application No. PCT/US2017/018527, dated Jun. 8, 2017.
International Search Report for corresponding International Application No. PCT/CN2015/000232, dated Jul. 1, 2015.
Japanese Notice of Reasons for Rejection, dated Jun. 13, 2017 with English machine translation, for corresponding Japan application No. 2017-033759.
Journal of Hubei Institute of Technology, Opimization on Ammonolysis in Manufacturing Method of Taurine, Year 2004, pp. 23-26, vol. 19, No. 1, Sum No. 66, Editorial Department of Journal of Hubei Polytechnic University, Wuhan, China (Year: 2004).
Liu Fuming, China Chemical Trade, Process Design of Taurine, Year 2013, p. 120, vol. 5, No. 6, China National chemical Center, Beijing City, China (Year 2013), http://chemmedia.com.cn/GotoBin/Select. DLL.
Notification of Reasons for Rejection issued by the Japan Patent Office for corresponding Japanese Patent Application No. 2017-505693, dated Mar. 27, 2018, with an English translation.
Objective Indicia Exhibit A: Excerpt from "Bulletin of Ministry of Environment Protection of China", Jan. 27, 2015, Nith English summary, and excerpt from "Environment Impact Assessment Report of 25,000l Year Taurine Plant of Hubei Grand Life Science and Technology Co. Ltd.", dated Jul. 24, 2017, with English summary.
Objective Indicia Exhibit B: "Production Flowchart of Taurine in Environmental Impact Assessment Report of Jiangying Huachang Food Additive Company", 2005, with English translation of flowchart.
Objective Indicia Exhibit C: "Production Flowchart of Taurine in Amended Environmental Impact Assessment Report of Jiangying Huachang Food Additive Company", 2017, with English translation of flowchart.
Objective Indicia Exhibit D: Selected Pages from Qiangjiang Yongan Pharmaceutical Co. Annual Reports 2012-2015, With partial English translations.
Objective Indicia Exhibit G: "Study of the Ammonolysis Reaction for Taurine" Liu 2015; Liu Fuming & Xie Liming, Shandong Chemical Industry, May, 2015, vol. 44, No. 5, pp. 27-28, 30, with English translations.
Objective Indicia Exhibit H: Liu 2013, Liu Fuming, China Chemical Trade Monthly Journal, Aug., 2013, vol. 5, Issue, 3, HGL Exhibit 1019.
Objective Indicia Exhibit I: Wu 2004, Wu Jiang & Guan Zailin J. , Journal of Hubei Polytechnic University, Feb. 2004, vol. 19, No. 1, pp. 23-26, HGL Exhibit 1016.
Objective Indicia filed with Response dated Jul. 25, 2019, 11 pages.
Objective Indicia filed with Response dated Jul. 30, 2019, 11 pages.
Office Action issued by the Canadian Intellectual Property Office for corresponding Canadian Patent Application No. 2,946,181, dated Mar. 26, 2018.
Patent Owner's Preliminary Response for Inter Partes Review of U.S. Pat. No. 9,428,450 IPR2018-01766, dated Jan. 11, 2019, 50 pages.
Patent Owner's Preliminary Response for Inter Partes Review of U.S. Pat. No. 9,428,451 IPR2018-01767, dated Jan. 14, 2019, 62 pages.
Patent Owner's Preliminary Response for Inter Partes Review of U.S. Pat. No. 9,573,890 IPR2018-01768, dated Jan. 16, 2019, 54 pages.

(56) References Cited

OTHER PUBLICATIONS

Patent Owner's Response for Inter Partes Review of U.S. Pat. No. 9,428,450, IPR2018-01766, dated Jul. 12, 2019, 56 pages.

Results for experiments conducted between May 14, 2019 and Jun. 30, 2019, Vitaworks Exhibits 2009—2065.

Robert E. Maleczka's 2nd Declaration in Support of Patent Owner's Response for Inter Partes Review of U.S. Pat. No. 9,428,450, IPR2018-01766, dated Jul. 12, 2019, 81 pages, Vitaworks Exhibit 2007.

Robert E. Maleczka's Declaration in Support of Patent Owner's Preliminary Response for Inter Partes Review of U.S. Pat. No. 9,428,450 IPR2018-01766, dated Jan. 11, 2019, 60 pages.

Robert E. Maleczka's Declaration in Support of Patent Owner's Preliminary Response for Inter Partes Review of U.S. Pat. No. 9,428,451 IPR2018-01767, dated Jan. 14, 2019, 75 pages.

Robert E. Maleczka's Declaration in Support of Patent Owner's Preliminary Response for Inter Partes Review of U.S. Pat. No. 9,573,890 IPR2018-01768, dated Jan. 16, 2019, 67 pages.

USPTO Final Office Action for corresponding U.S. Appl. No. 16/030,605 dated Jan. 30, 2019.

USPTO Non-Final Office Action for corresponding U.S. Appl. No. 14/120,046 dated Aug. 26, 2015.

USPTO Non-Final Office Action for corresponding U.S. Appl. No. 14/120,651 dated Mar. 15, 2016.

USPTO Non-Final Office Action for corresponding U.S. Appl. No. 15/228,539 dated Oct. 17, 2016.

USPTO Non-Final Office Action for corresponding U.S. Appl. No. 15/228,568 dated Oct. 5, 2016.

USPTO Non-Final Office Action for corresponding U.S. Appl. No. 15/870,844 dated May 10, 2018.

USPTO Non-Final Office Action for corresponding U.S. Appl. No. 16/030,605 dated Aug. 9, 2018.

USPTO Notice of Allowance for corresponding U.S. Appl. No. 15/870,844 dated Jun. 15, 2018.

Wu Jiang, Guan Zailin, "Optimization on Ammonolysis in Manufacturing Method of Taurine", Journal of Hubei Polytechnic University, 2004, vol. 19, No. 1, pp. 23-26. (English translation included).

\* cited by examiner

PROCESS FOR PRODUCING TAURINE

CROSS REFERENCE TO RELATED APPLICATIONS

This application is a continuation-in-part of the application Ser. No. 15/894,382, filed on Feb. 12, 2018, which is a continuation-in-part of the application Ser. No. 15/832,667, filed on Dec. 5, 2017, now U.S. Pat. No. 10,112,894, which is a continuation-in-part of the application Ser. No. 15/495,297, filed on Apr. 24, 2017, now U.S. Pat. No. 9,926,265, which is a continuation-in-part of the application Ser. No. 15/366,798, filed on Dec. 1, 2016, now U.S. Pat. No. 9,815,778, which is a continuation-in-part application of Ser. No. 15/268,071, filed on Sep. 16, 2016, now U.S. Pat. No. 9,745,258, all of which are incorporated herein by reference.

TECHNICAL FIELD

The present invention relates to a process for the production of taurine from ammonium taurinate by thermal decomposition to taurine and ammonia. Ammonium taurinate is prepared by catalytic ammonolysis of ammonium isethionate, by catalytic hydrogenation of 2-nitroethanesulfonate, by the reaction of aziridine with ammonium bisulfite, by the reaction of 2-oxazolidinone with ammonium bisulfite, or by mixing alkali taurinate with an ammonium salt.

BACKGROUND OF THE INVENTION

Taurine can be referred to as 2-aminoethanesulfonic acid and is one of the amino sulfonic acids found in the tissues of many animals. Taurine is an essential natural compound that promotes human neonatal development, brain development, and heart function. Taurine finds wide applications as a dietary supplement and as a pharmaceutical in the treatment of cardiovascular disease, elevated blood pressure, hepatic disorders, diabetes, and dermatological conditions. Taurine is used as a key ingredient in energy drinks to improve performance. In addition, taurine may be used as a plant growth stimulator to increase crop yield and plant biomass.

Taurine is currently produced in an amount of over 60,000 tons per year from either ethylene oxide or monoethanolamine. At the present time, most taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hours at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD 219 023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO 01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

U.S. Pat. Nos. 9,428,450, 9,428,451, 9,573,890, and 9,598,357 overcome some of the problems in the known ethylene oxide process by inhibiting the formation of the byproducts of the ammonolysis reaction of alkali isethionate, alkali ditaurinate and alkali tritaurinate, and converting the byproducts into alkali taurinate. The overall yield of the cyclic process for producing taurine from sodium isethionate is increased to from 85% to nearly quantitative.

CN 104945289A and CN 105732440A describe recycling of the mother liquor, which contains sodium ditaurinate and sodium taurinate, during the ammonolysis of sodium isethionate in the production of taurine to increase the yield and to reduce discharge of waste.

U.S. Pat. No. 8,609,890 discloses a cyclic process of using isethionic acid or sulfur dioxide to neutralize alkali taurinate to producing taurine and to regenerate alkali isethionate. U.S. Pat. No. 9,108,907 further discloses a process of using isethionic acid prepared from ethanol to neutralize alkali taurinate to regenerate alkali isethionate. The aim is to reduce or eliminate the use of sulfuric acid as an acid agent in the production of taurine.

U.S. Pat. No. 9,061,976 discloses an integrated production scheme by using sulfur dioxide as an acid and by converting the byproducts of the ammonolysis reaction, alkali ditaurinate and alkali tritaurinate, to alkali taurinate.

The overall production yield is increased to greater than 90% and alkali sulfate is eliminated from the production process. One drawback of this process is the use of gaseous sulfur dioxide, which imparts a slight smell on the product. Another significant drawback is that the taurine product from this process may contain trace amount of alkali sulfite which could be an allergen for certain people.

U.S. Pat. No. 9,593,076 discloses a cyclic process for producing taurine from isethionic acid in a high overall yield of greater than 90% to nearly quantitative, while generating no inorganic salt as byproducts. Similarly, CN 106008280A describes the use of isethionic acid to neutralize sodium taurinate and to regenerate sodium isethionate. However, the starting material, isethionic acid, is difficult to obtain commercially and is produced by a costly process of bipolar membrane electrodialysis of alkali isethionate.

U.S. Pat. No. 9,850,200 discloses a process for producing taurine by using an ammonium salt to react with alkali taurinates to yield taurine. In particular, ammonium bisulfite, ammonium sulfite, or their mixture is used to produce taurine and to regenerate a mixture of alkali bisulfite and alkali sulfite. Other suitable ammonium salts are selected from the group of ammonium sulfate, ammonium bisulfate, ammonium chloride, ammonium bromide, ammonium nitrate, ammonium phosphate, ammonium hydrogen phosphate, ammonium dihydrogen phosphate, ammonium carbonate, ammonium bicarbonate, ammonium carboxylate, ammonium alkyl sulfonate, ammonium aryl sulfonate, and a mixture of two or more thereof.

CN 101717353A describes a process of preparing taurine by (1) reacting ethylene oxide with ammonium sulfite to yield ammonium isethionate and ammonia; (2) ammonolysis of the obtained product to ammonium taurinate; (3) acidifying with sulfuric acid to afford taurine. However, repeated attempts fail to produce any taurine under disclosed conditions.

JPS63243066 discloses a process of preparing taurine by reacting aziridine or ethyleneimine with an aqueous solution of sulfurous acid and adjusting the pH of the solution with a base. Because of limited solubility of sulfurous acid, the reaction is carried out under very dilute condition and the process is not economical.

JPH04352760 discloses a process of preparing taurine by absorbing gaseous aziridine with a solution of excess ammonium bisulfite or alkali bisulfite. Taurine or alkali taurinate is separated by distilling off water under vacuum and the product is isolated by washing with an alcohol.

JPH08268995 describes a cyclic process of preparing taurine from aziridine by first reacting aziridine with an excess of alkali bisulfite to form alkali taurinate, which is neutralized with sulfur dioxide to taurine and to regenerate alkali bisulfite. The direct contact of sulfur dioxide with taurine imparts a slight foul smell on the final product taurine.

Chen et al describe a method of preparing taurine by reacting aziridine with an excess of ammonium bisulfite (Zhejiang Chemical Industry, 2011, Vol. 42, No. 5, pp 5, 18-20). However, the method gives only a moderate yield of about 75% and a large amount of mother liquor that is difficult to dispose of.

CN 103613517A discloses a process for producing taurine by reducing 2-nitroethanesulfonate sodium salt to sodium taurinate, which is neutralized with sulfuric acid to taurine and sodium sulfate. The reduction is carried out preferably by hydrogenation in the presence of a catalyst such as Raney Ni or Pd/C.

CN 105693559A describes a process of producing taurine from sodium taurinate by replacing sulfuric acid with carbon dioxide to produce taurine and coproduce sodium bicarbonate, which is a useful commodity.

CN 106588704A discloses a cyclic process that improves the CN 103613517A process by first reacting 2-nitroethanol with ammonium bisulfite to form ammonium 2-nitroethanesulfonate, which is reduced to ammonium taurinate by catalytic hydrogenation. Sulfur dioxide is then used to neutralize ammonium taurinate to taurine and to regenerate ammonium bisulfite. One drawback of this process is the use of gaseous sulfur dioxide, which is obnoxious and imparts a slight smell on the product. Another significant drawback is that the taurine product from this process may contain trace amount of alkali sulfite which could be an allergen for certain people.

U.S. Pat. No. 4,444,694 discloses a process for the preparation of metal salts of 2-aminoethanesulfonic acid, which comprises the reaction of 2-oxazolidinone with alkali sulfite, alkali bisulfite, or their mixture. The reaction yield is usually high, greater than 90%. A major drawback of the process is the use of an acid to neutralize alkali taurinate, thus generating a large quantity of inorganic salt as byproduct.

It is an object of the present invention to overcome the disadvantage of the known processes for the production of taurine and to provide, in addition, advantages, which will become apparent from the following description.

It is another object of the present invention to disclose a process for the production of taurine from ammonium isethionate in a high overall yield (i.e., greater than 90% to nearly quantitative) without generating any inorganic salt as byproduct.

It is a further object of the present invention to disclose a process for producing taurine by thermal decomposition of ammonium taurinate to taurine and ammonia. Additional acid is eliminated from neutralizing ammonium taurinate, thus avoiding the formation of inorganic salt byproducts.

The starting material, ammonium isethionate, can be readily and economically produced by reacting ethylene oxide with ammonium bisulfite according to prior art, e.g., U.S. Pat. Nos. 5,646,320 and 5,739,365.

According to the process of the present invention, a solution of alkali isethionate or regenerated alkali isethionate, alkali ditaurinate, and alkali tritaurinate is mixed with an excess of ammonia and is subjected continuously to the ammonolysis reaction to form a mixture of alkali taurinate, alkali ditaurinate, and alkali tritaurinate, in the presence of one or more catalysts. After ammonium isethionate is added to the ammonolysis solution to form ammonium taurinate and alkali isethionate, excess ammonia and ammonia released from a thermal decomposition of ammonium taurinate are removed to obtain a crystalline suspension of taurine in a solution of alkali isethionate, alkali ditaurinate, and alkali tritaurinate. Upon the solid-liquid separation of taurine, the mother liquor is directly recycled to the ammonolysis step.

The advantage of using ammonium isethionate as a starting material becomes apparent in that no isolation of alkali salt as a byproduct is necessary after the separation of crystalline taurine from the mother liquor containing alkali isethionate, alkali ditaurinate, and alkali tritaurinate. Moreover, the final product, taurine, does not contain any inorganic salt, such as alkali sulfate or alkali halide, as impurity.

DESCRIPTION OF THE INVENTION

The present invention relates to a cyclic process for the production of taurine from ammonium isethionate in a high overall yield of greater than 90% to nearly quantitative without generating any inorganic salt as byproduct.

The starting material, ammonium isethionate is produced by reacting ethylene oxide with ammonium bisulfite according to the following equation:

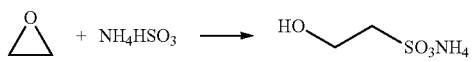

Ammonium isethionate, produced in a solution, can be used directly for the production of taurine. Preferably, ammonium isethionate is purified by concentrating the solution to obtain crystalline materials. When solid ammonium isethionate is used in the production of taurine, the quality of taurine produced is improved and almost no purge of mother liquor is required from the cyclic process.

The process according to the present invention starts with mixing a solution of alkali isethionate or regenerated alkali isethionate, alkali ditaurinate, and alkali tritaurinate, with an excess of ammonia. The presence of alkali ditaurinate and alkali tritaurinate in the reaction solution inhibits the formation of byproducts, increases the production yield, and greatly reduces or eliminates the waste discharge from the production process. The alkali metals are lithium, sodium, or potassium.

The ammonolysis reaction is carried out at a temperature from 160° C. to 280° C. under the pressure from autogenous to 260 bars for 1 to 6 hours.

After the ammonolysis reaction, excess ammonia is dispelled from the reaction solution and reclaimed for reuse. Ammonium isethionate is added to the ammonolysis solution before or after the removal of excess ammonia to react with alkali taurinates to yield alkali isethionate and ammonium taurinate.

Ammonium taurinate is decomposed to taurine by heating and removing ammonia from the solution. The temperature for decomposing ammonium taurinate is from 75° C. to 150° C., preferably from 90 to 120° C., most preferably from 95 to 110° C. Removal of ammonia released from the decomposition of ammonium taurinate can be carried out under reduced, normal, or increased pressure.

The amount of ammonium isethionate in relation to alkali taurinate in the ammonolysis solution can be from 0.1 to 10 on the molar basis. Preferably, the molar ratio is from 0.5 to 1.5, more preferably from 0.9 to 1.1, and most preferably from 0.95 to 1.05. When the ratio is lower than the equivalent, the final pH after ammonia removal tends to be higher than 7 and more taurine will remain in the solution. When the ratio is greater than equivalent, the final pH is in the desirable range of 5 to 6, but additional alkali hydroxide will be consumed during the ammonolysis stage.

The reaction of alkali taurinate formed in the ammonolysis stage with ammonium isethionate proceeds according to the following equation:

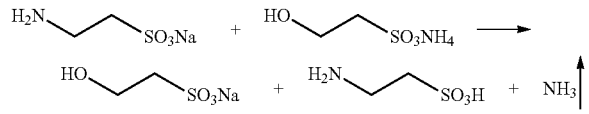

After complete removal of ammonia, the strongly basic solution becomes neutral to yield a crystalline suspension of taurine in a solution of alkali isethionate, alkali ditaurinate, and alkali tritaurinate. The final pH can also be fine-adjusted with the mixed acids of isethionic acid and ditaurine, produced by the bipolar membrane electrodialysis of the mother liquor containing alkali isethionate and alkali ditaurinate. The initial suspension is optionally concentrated, then cooled to crystallize taurine in a solution of alkali ditaurinate, alkali tritaurinate, and alkali isethionate. Taurine is obtained by means of solid-liquid separation.

After separation of taurine, the mother liquor, containing regenerated alkali isethionate, alkali ditaurinate, and alkali tritaurinate, is saturated with ammonia and is subjected to the ammonolysis reaction.

It becomes apparent that alkali in the reaction system is continuously recycled in the process and only ammonium isethionate is transformed to taurine. The net reaction of the cyclic process is:

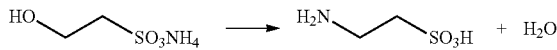

Useful and effective catalysts for the ammonolysis reaction are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate in the presence of alkali ditaurinate and alkali tritaurinate can be one component or a combination of two or more components. Preferable catalysts are alkali hydroxide and the most preferable catalyst is sodium hydroxide.

The amount of catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

As a catalyst, alkali hydroxide is introduced into the reaction system and additional ammonium isethionate is required to neutralize the strong base. The result is an increased accumulation of alkali in the cyclic process. It is thus preferable to generate the alkali hydroxide within the production unit. A convenient way is to split a mixture of alkali isethionate and alkali ditaurinate in the mother liquor into an acidic component, a mixture of isethionic acid and ditaurine, and an alkali hydroxide component, by using bipolar membrane electrodialysis. The mixed acidic solution of isethionic acid and ditaurine is used as an acid after the ammonolysis while alkali hydroxide is used as a catalyst for the ammonolysis reaction.

The cyclic process according to the present invention affords taurine in a yield of greater than 90%, to nearly quantitative, and generates no waste other than a small amount of purge from the cyclic system.

Moreover, the taurine product produced according to the present invention does not contain any inorganic contaminants, such as alkali sulfate or alkali halide, which is present in the commercially available products from existing industrial processes.

Aziridine undergoes a ring-opening reaction with sulfurous acid or a salt of bisulfite or sulfite to form taurine or alkali taurinate, which is neutralized with an acid or an excess of bisulfite salts. The present invention discloses that ammonium taurinate, prepared by reacting aziridine with ammonium bisulfite, ammonium sulfite, or their mixture, can be decomposed to taurine by heating and removing ammonia from the reaction system, according to the following reaction:

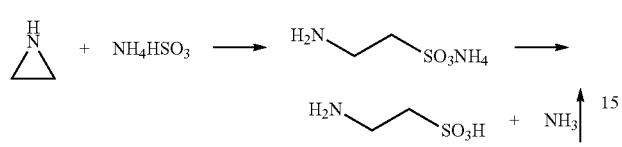

The process according to the present invention overcomes disadvantages in using sulfur dioxide, sulfurous acid, or an acid to produce taurine.

The reaction of aziridine with ammonium bisulfite, ammonium sulfite, or their mixture is highly exothermic and external cooling is necessary to maintain the reaction temperature from 0° C. to 100° C., preferably from 20° C. to 80° C., more preferably from 20° C. to 60° C., and most preferably from 25° C. to 45° C.

The aziridine, suitable for the present process, can be gaseous, neat liquid, or aqueous solution. The aziridine is prepared by gaseous dehydration of monoethanolamine in the presence of catalyst, by alkali hydroxide treatment of 2-aminoethylsulfonate ester, or by ammonolysis of 1,2-dichloroethane. Aziridine can be used in a purified form or as a crude product from the production process. Alkali hydroxide is selected from lithium hydroxide, sodium hydroxide, potassium hydroxide, or cesium hydroxide.

The molar ratio of aziridine to sulfite can be varied from 0.1 to 1, preferably from 0.5 to 1, more preferably from 0.8 to 1.0, and most preferably 0.9 to 0.95. A slight excess of sulfite is necessary for a complete reaction of aziridine to yield ammonium taurinate. Presence of even trace amount of aziridine in the reaction solution must be destroyed in the product stream of taurine as aziridine is quite toxic and carcinogenic to be a contaminant for a food product.

After the ring-opening reaction of aziridine with ammonium bisulfite is complete, ammonium taurinate is decomposed to taurine and ammonia by heating and the ammonia released from the reaction is expelled from the solution. Preferably, ammonia is absorbed with sulfur dioxide to produce ammonium bisulfite, which is used to react with aziridine. FIG. 2 illustrates the cyclic nature of the process according to the present invention.

After the separation of taurine by solid-liquid separation, the mother liquor is mixed with ammonium bisulfite, ammonium sulfite, or their mixture to prepare a solution to further react with aziridine. In addition, the mother liquor is also used to absorb ammonia and sulfur dioxide to prepare a solution of ammonium bisulfite, ammonium sulfite, or their mixture, which is then reacted with aziridine to complete the cyclic process. As the reaction between aziridine and sulfite generates negligible amount of byproduct, little purge of the mother liquor is required in the cyclic process.

The process according to the present invention yields taurine in a yield of greater than 90% to quantitative on the molar basis of aziridine.

There are various methods for producing taurine where ammonium taurinate is formed as in intermediate. Ammonium taurinate formed by any of these methods can be used according to the present invention, For example, in one embodiment of the present invention, when ammonium 2-nitroethanesulfonate is reduced by hydrogenation in the presence of a catalyst, ammonium taurinate is formed. The process according to the present invention is to decompose this intermediate to taurine and ammonia according to the following reaction scheme:

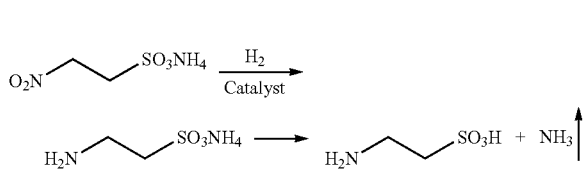

The advantage of the present invention becomes apparent in that no acids, such as sulfuric acid, carbon dioxide, sulfur dioxide, or sulfurous acid, are required to produce taurine. The process according to the present invention is greatly simplified, since no salt as byproduct is formed.

The starting material, ammonium 2-nitroethanesulfonate, can be prepared by processes known in the prior art. For example, the reaction of 2-nitroethanol or nitroethylene with ammonium bisulfite, ammonium sulfite or their mixture results in the formation of ammonium 2-nitroethanesulfonate in nearly quantitative yield.

The reduction of ammonium 2-nitroethanesulfonate to ammonium taurinate can be carried out with methods known in the prior art for the reduction of nitro group. Preferably, the reduction is performed with catalytic hydrogenation in the presence of a hydrogenation catalyst. Suitable catalysts are Raney Ni and Pd/C. The hydrogenation is carried out in aqueous solution, or aqueous alcohol solution, or in a lower alcohol. A lower alcohol is selected from the group of methanol, ethanol, propanol, isopropanol, ethylene glycol, propylene glycol, glycerol, and a mixture to two or more thereof.

After the reduction is complete, solid catalyst is filtered off to provide a solution of ammonium taurinate, which is decomposed to taurine and ammonia by heating and the ammonia released from the reaction is expelled from the solution. Preferably, ammonia is absorbed with sulfur dioxide to produce ammonium bisulfite, ammonium sulfite, or their mixture. After cooling, taurine is crystallized and separated by solid-liquid separation.

Decomposition of ammonium taurinate to taurine is carried out by heating the solution to a temperature from 60° C. to 150° C., at reduced, normal or increased pressure. Preferably, the decomposition is performed at a temperature from 80° C. to the boiling point of the solution at normal pressure, so that no special equipment is required.

The process according to the present invention yields taurine in a yield of from 90% to quantitative on the basis of ammonium 2-nitroethanesulfonate. Little byproduct or no byproduct is isolated in the process.

In another embodiment of the present invention, ammonium taurinate is prepared by the reaction of 2-oxazolidinone with ammonium bisulfite, ammonium sulfite, or their mixture. The process for producing taurine from 2-oxazolidinone according to the process of present invention can be described as follows:

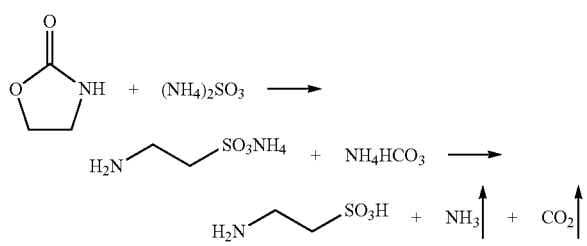

The advantage of the present invention becomes apparent in that no acids, such as sulfuric acid, carbon dioxide, sulfur dioxide, or sulfurous acid, are required to produce taurine. The process according to the present invention is greatly simplified, since no salt as byproduct is formed.

The starting material of the present process, 2-oxazolidinone can be prepared by one of the methods known in prior art. For example, 2-oxazolidinone can be conveniently and economically produced by the reaction of monoethanolamine with urea. It can also be prepared by the oxidative addition reaction of monoethanolamine with carbon monoxide. 2-Oxazolidinone can be used in a purified state or used as a crude product from the production process.

The reaction of 2-oxazolidinone with ammonium sulfite, ammonium bisulfite, or their mixture is carried out in a molar ratio from 1.0:0.9 to 1.0:10, preferably 1.0:5.0, more preferably 1.0:2.0, most preferably 1.0:1.2. The reaction is carried out in a pH range from 5.0 to 9.0, preferably from 6.0 to 8.0, more preferably from 6.5 to 7.5. When the initial pH is above 9.0 or below 5.0, 2-oxazolidinone is partially hydrolyzed to monoethanolamine during the reaction.

The reaction is usually carried out as an aqueous solution. It is also possible to add water-miscible organic solvent to the reaction medium. Suitable solvents are, but not limited to, methanol, ethanol, propanol, isopropanol, butanol, isobutanol, 2-butanol, tetrahydrofuran, dimethylformamide, dimethylacetamide, N-methylpyrrolidone, tetramethylurea, acetone, acetonitrile, dimethylsulfoxide, ethylene glycol, propylene glycol, diethylene glycol, glycerine, and a mixture of two or more thereof.

The reaction of 2-oxazolidinone with ammonium sulfite, ammonium bisulfite, or their mixture can be carried out in an open vessel from a temperature of 60° C. to refluxing temperature of the solution. If the reaction is carried out under normal pressure in a reactor equipped with a condenser, some of ammonium bicarbonate and ammonium bisulfite may decompose and deposit in the condenser, thus clogging the condenser. Therefore, the reaction is preferably carried out in a closed vessel such as an autoclave from a temperature of 60° C. from 160° C. under a pressure from autogenous to 80 bars. Preferably, the reaction is carried out at a temperature from 70° C. to 140° C., more preferably from 80° C. to 130° C., most preferably from 90° C. to 120° C.

After the reaction is completed as shown from the disappearance of 2-oxazolidinone in the solution, the solution is heated to decompose ammonium taurinate and ammonium bicarbonate or ammonium carbonate to taurine, ammonia, and carbon dioxide. Ammonia and carbon dioxide are removed from the solution and recovered as an aqueous solution, which can be used to absorb sulfur dioxide to regenerate ammonium sulfite or ammonium bisulfite. As ammonia and carbon dioxide are dispelled from the solution, a solution of taurine is obtained. The taurine solution is optionally concentrated by evaporation. After cooling, taurine is crystallized and separated by solid-liquid separation such as filtration or centrifuge. The mother liquor can be recycled into the reaction for further use of excess ammonium sulfite.

The process for producing taurine from 2-oxazolidinone according to the present invention gives a yield of more than 90% to nearly quantitative.

In a further embodiment of the present invention, ammonium taurinate is obtained by subjecting ammonium isethionate to an ammonolysis reaction in the presence of at least one catalyst at a temperature from 150° C. to 500° C. under a pressure from autogenous to 350 bars. Removal of the excess ammonia and ammonia released from the decomposition of ammonium taurinate to taurine and ammonia can be carried out by heating or by stripping with steam. After complete removal of ammonia, the strongly basic solution becomes neutral to yield a crystalline suspension of taurine in a solution of unreacted ammonium isethionate, ammonium ditaurinate, and ammonium tritaurinate. The initial suspension is optionally concentrated, then cooled to crystallize taurine. Taurine is obtained by means of solid-liquid separation.

The reaction according to the present invention can be described as follows:

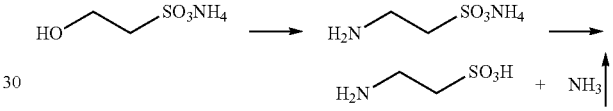

Effective catalysts for the ammonolysis reaction are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, potassium sulfite, and a mixture of two or more thereof.

In comparison to alkali isethionate, ammonium isethionate can only be converted to ammonium taurinate at much higher temperature, if this class catalyst is used. The ammonolysis reaction may be carried out from 200° C. to 500° C., preferably from 260° C. to 400° C., more preferably from 280° C. to 380° C., most preferably from 300° C. to 350° C.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

More effective catalysts for the ammonolysis of ammonium isethionate are found among transition metal salts. In particular, transition metal salts are selected from IB, VB, VIB, VIIB, or VIIM in the periodic table. These salts are, but not limited to, V(II), V(III), V(IV), V(V), Cr(II), Cr(III), Cr(VI), Mo(VI), W(VI), Mn(II), Mn(III), Mn(IV), Mn(VII), Fe(II), Fe(III), Ru(II), Ru(III), Co(II), Co(III), Ni(II), Cu(I), Cu(II), Ag(I), and a mixture of two or more thereof. Specific salts are, but not limited to, ammonium, lithium, sodium, potassium, magnesium, calcium, barium salts of molybdate, tungstate, polyoxomolybdate, or polyoxotungstate. The anions for salts of Mn(II), Mn(III), ferrous, ferric, cupric, cuprous, Ru(II), Ru(III), Co(II), Co(III), Ni(II) or Ag(I) are selected from the group consisting of oxide, hydroxide, fluoride, chloride, bromide, iodide, sulfate, bisulfate, carbonate, sulfite, bicarbonate, nitrate, phosphate, alkyl carboxylate, aryl carboxylate, alkyl sulfonate, aryl sulfonate, molybdate, tungstate, polyoxomolybdate, and polyoxotungstate. A mixture of two or more of these salts can be used as an effective catalyst. The ammonolysis reaction may be carried out from 150° C. to 350° C., preferably from 160° C. to 300° C., more preferably from 170° C. to 240° C., most preferably from 180° C. to 220° C.

Particularly effective catalysts are found among the hydrogenation catalysts for the ammonolysis reaction of ammonium isethionate. These catalysts are based on nickel, cobalt, copper, or platinum group metals of platinum, palladium, ruthenium, rhodium, osmium, iridium, and rhenium. For example, suitable catalysts are Raney nickel, Raney copper, Pd/C, or Ru/C. The catalytic activity of these catalysts is greatly enhanced in the presence of hydrogen or one of hydrogen donors such as formic acid or a secondary alcohol. The ammonolysis reaction may be carried out from 150° C. to 350° C., preferably from 160° C. to 300° C., more preferably from 170° C. to 240° C., most preferably from 180° C. to 220° C.

After the reaction, the catalyst is separated from ammonium taurinate by methods known in prior art, in general, solid-liquid separation. The solution of ammonium taurinate is heated to remove excess ammonia and to decompose ammonium taurinate to taurine, which is crystallized upon cooling and separated by solid-liquid separation. The mother liquor after taurine separation may be recycled to the ammonolysis step to increase the yield of taurine from ammonium isethionate. The cyclic process according to the present invention for producing taurine from ammonium isethionate can achieve a yield of greater than 85% to nearly quantitative.

The advantage according to the present invention becomes apparent in that no alkali recycling is performed in the process, thus the reaction mass efficiency is greatly increased.

The process according to the present invention can be carried out discontinuously, semi-continuously, and continuously.

EXAMPLES

Figure 1:
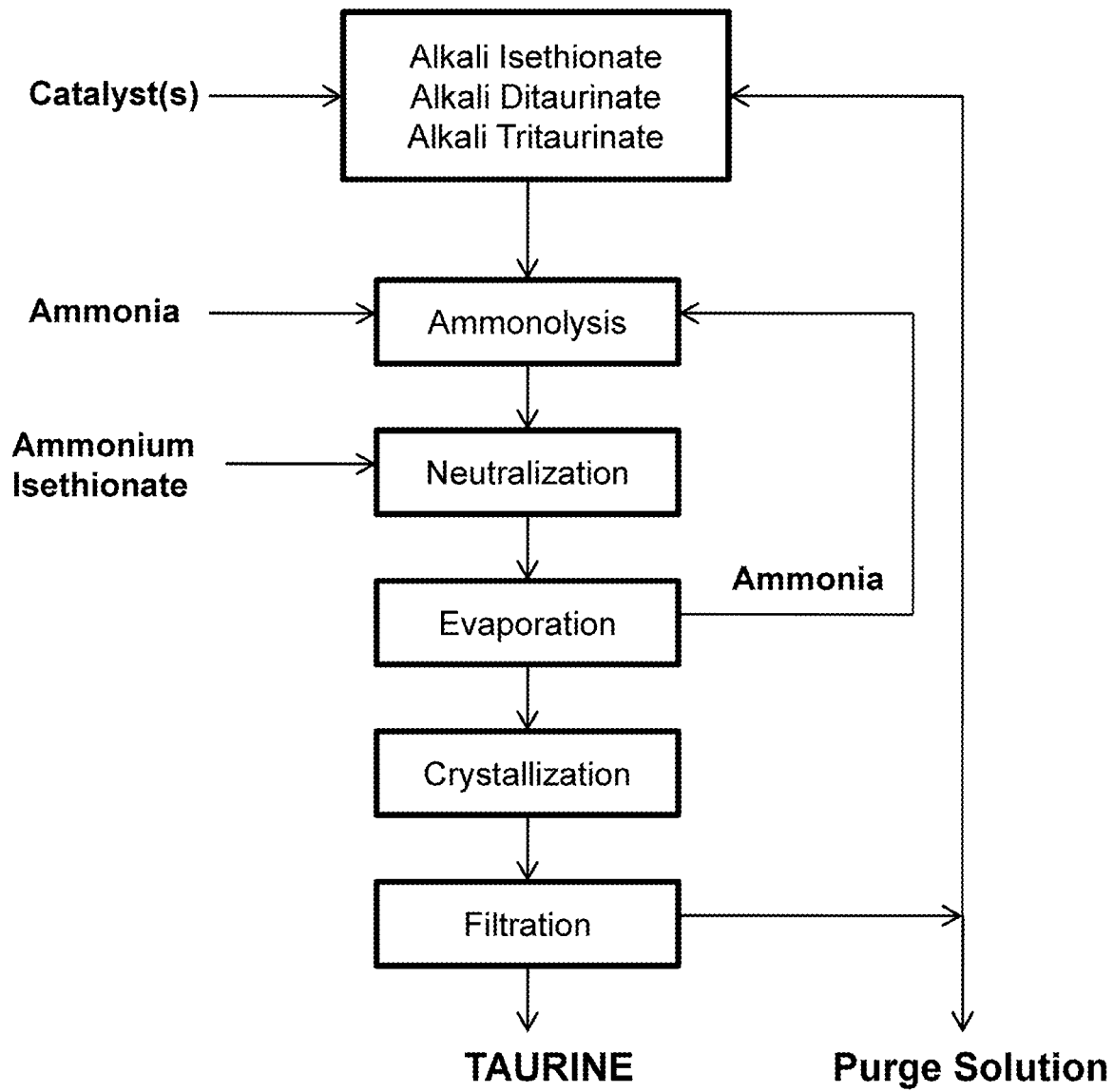
FIG. 1 illustrates one embodiment of a flowchart for producing taurine from ammonium isethionate.
Figure 2:
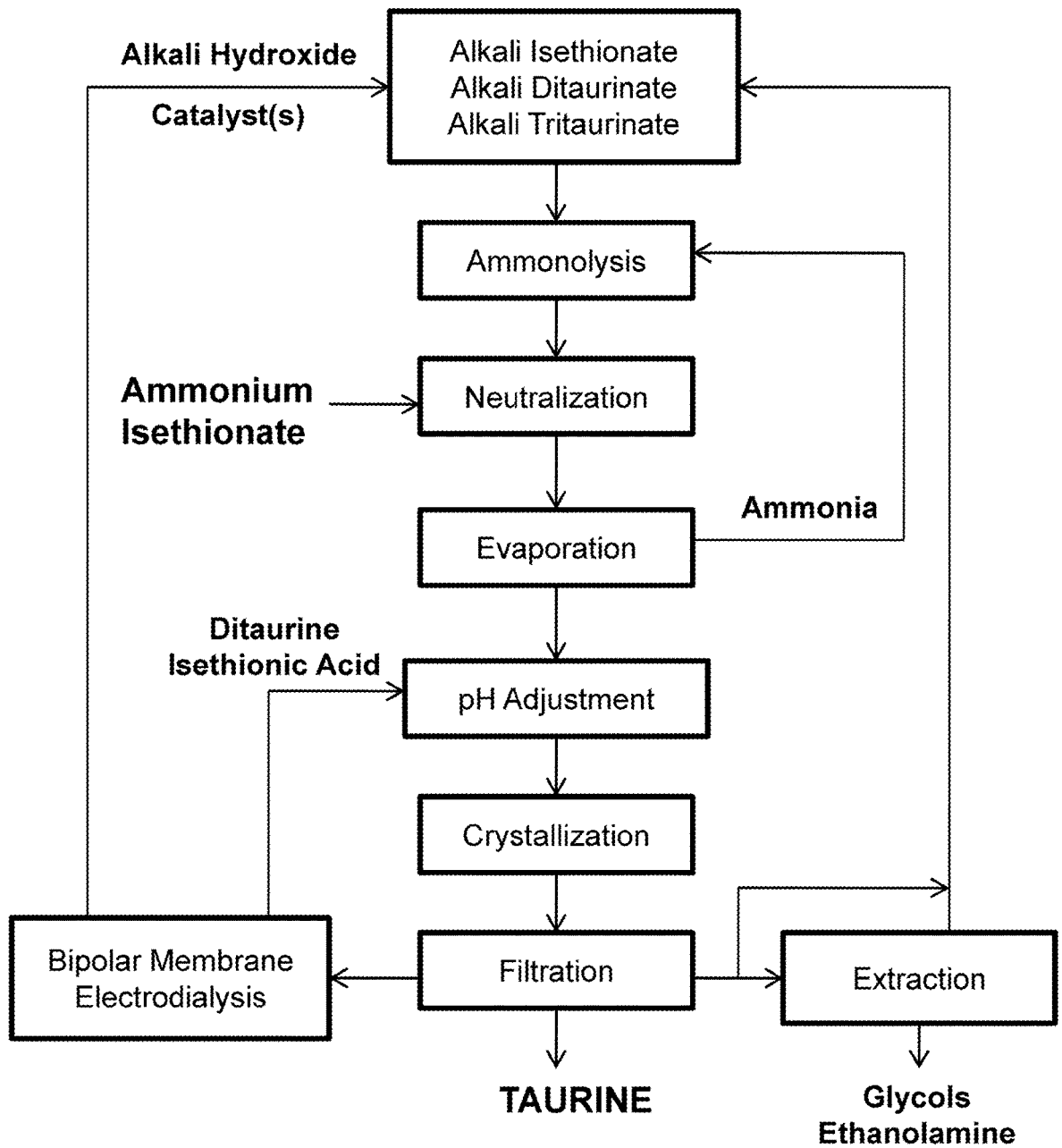
FIG. 2 illustrates another embodiment of a flowchart for producing taurine from ammonium isethionate.
Figure 3:
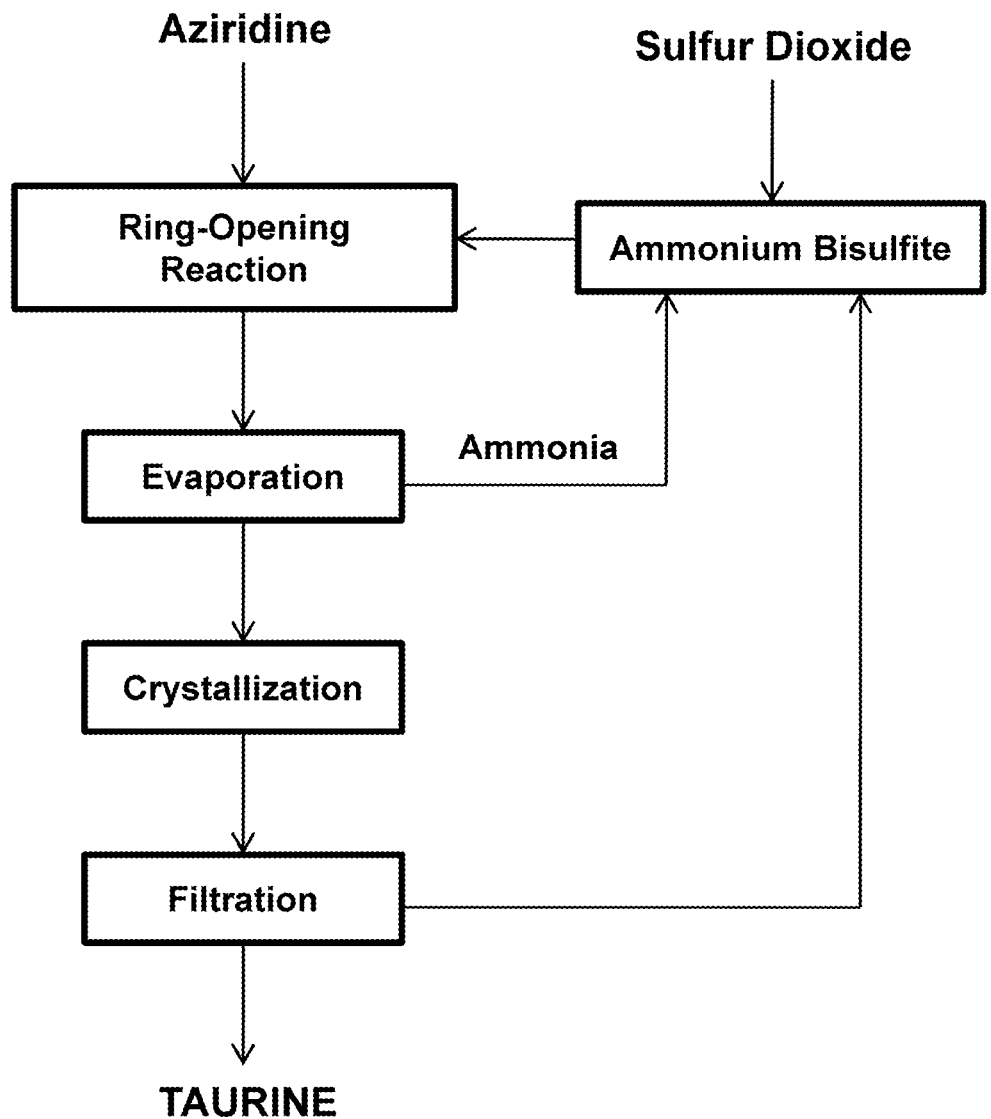
FIG. 3 illustrates one embodiment of a flowchart for producing taurine from aziridine.

The following examples illustrate the practice of this invention but are not intended to limit its scope.

Example 1

To a 2-L autoclave are added 1200 mL of 24% ammonia solution, 296 g of sodium isethionate, and 2 g of sodium hydroxide. The solution is heated to 260° C. for 2 hours under autogenous pressure. After cooling, 286.2 g of ammonium isethionate is added and ammonia is removed by boiling to bring the pH of the solution to pH 6.5. After heating to remove excess ammonia, concentrating and cooling to room temperature, a suspension of crystalline taurine is obtained. Taurine is recovered by filtration and dried to 189.3 g. Taurine is recovered in a yield of 75.7%.

Example 2

To the mother liquor of Example 1 is added 340 g of gaseous ammonia and total volume is adjusted to 1500 mL with deionized water, followed by addition of 12.4 g of sodium hydroxide. The solution is placed in a 2-L autoclave and is subjected to ammonolysis reaction and treatment with ammonium isethionate as described in Example 1.

Taurine, 241.2 g after drying, is obtained in a yield of 96.2% on the basis of ammonium isethionate used.

Examples 3 to 7

The mother liquor after isolation of taurine, after being saturated with ammonia, is repeatedly subjected to the ammonolysis reaction in the presence of 15 g of sodium hydroxide 5 times for an overall yield of taurine of 96.4% on the basis of ammonium isethionate used.

Example 8

To 240 g of a 50% solution of ammonium bisulfite was added dropwise 143.6 g of a 35% aqueous solution of aziridine, prepared by distilling a sodium hydroxide solution of 2-aminoethylsulfonate ester, while the temperature was maintained between 35 to 45° C. The initial pH of ammonium bisulfite was at 4.6 and the final pH of the solution became 9.8. After being stirred at the same temperature for 2 additional hours, the solution was heated to reflux to decompose ammonium taurinate to taurine and ammonia. After cooling, taurine crystallized from the solution and the pH of the crystalline suspension became 6.5.

After filtration and drying, 108 g of taurine was obtained as a white crystalline solid and 14 g of taurine remained in the mother liquor. The total yield was 97.6% on the basis of aziridine.

Example 9

To 1 L flask were added 500 mL of deionized water, 172 g of ammonium 2-nitroethanesulfonate, and 10 g of Raney Ni. The flask was mounted to a Parr shaker and purged with hydrogen three times and the hydrogenation was continued until no more absorption of hydrogen was observed. The suspension was filtered to remove Raney Ni catalyst to provide a clear solution, which was heated to boiling to a total volume of about 500 mL. No ammonia was observed to escape at the end of boiling and the pH of the solution was 6.8. Upon cooling, massive crystallization of taurine was obtained. After filtration and drying, 114 g of taurine was obtained as white crystalline material and 9 g of taurine remained in the mother liquor. The overall yield of taurine from ammonium 2-nitroethanesulfonate was 98.1%.

Example 10

To a 1-L autoclave was added 500 mL of deionized water and 150 g of ammonium sulfite dehydrate and the pH of the solution was lowered to 7.5 by bubbling carbon dioxide. After 88.5 g of 2-oxazolidinone was dissolved in the solution, the autoclave was purged was nitrogen and heated to 110° C. for 5 hours. The solution was then boiled to remove ammonia and carbon dioxide and concentrated. Upon cooling, massive amount of crystalline taurine was formed. The crystalline suspension was further cooled to 10° C. and filtered. 102 g of taurine was obtained as white crystalline material and 11 g of taurine remained in the mother liquor. The overall yield of taurine from 2-oxazolidinone was 90.4%.

Example 11

Into a 25 mL of stainless tube was added 20 mL of a solution containing 25% ammonia, 4 g of ammonium isethionate, and 0.2 g of sodium carbonate. The sealed tube was then immersed in a salt bath at 425° C. for 2 hours. The tube was then cooled to room temperature and the content assayed for taurine. The conversion rate of ammonium isethionate to ammonium taurinate was found to be 67%.

Example 12

Into a 100 mL of autoclave was added 75 mL of a solution containing 25% ammonia, 15 g of ammonium isethionate, 0.5 g of ferric chloride and 0.5 g of ammonium tungstate. The autoclave was heated to 225° C. for two hours. After cooling to room temperature, the content was assayed for taurine. The conversion rate of ammonium isethionate to ammonium taurinate was found to be 72%.

Example 13

Into a 1 L of autoclave equipped with a stirrer was added 500 mL of a solution containing 25% ammonia and 50 g of ammonium isethionate and 1.0 g of 10% Pd—C catalyst. The autoclave was purged with hydrogen three times to replace air. It was then heated to 180° C. and kept stirring for 2 hours. After cooling to room temperature and replacing hydrogen with nitrogen. The mixture was filtered to obtain a colorless solution, which was boiled to remove ammonia and to decompose ammonium taurinate. After the solution was concentrated to 170 mL and cooled on ice to form a mass of crystalline taurine. After filtration and drying, 34.5 g of taurine was obtained as white crystalline solid.

It will be understood that the foregoing examples, drawing, and explanation are for illustrative purposes only and that various modifications of the present invention will be self-evident to those skilled in the art. Such modifications are to be included within the spirit and purview of this application and the scope of the appended claims.

What is claimed is:

1. A process for producing taurine from 2-oxazolidinone, comprising:
    (a) reacting 2-oxazolidinone with ammonium sulfite, or ammonium bisulfite, or a mixture of ammonium sulfite and ammonium bisulfite in an aqueous solution to form ammonium taurinate and ammonium bicarbonate;
    (b) decomposing ammonium taurinate and ammonium bicarbonate to taurine, ammonia, and carbon dioxide by heating and removing ammonia and carbon dioxide to obtain a crystalline suspension of taurine; and
    (c) separating taurine by means of solid-liquid separation.

2. The process according to claim 1, wherein the molar ratio of 2-oxazolidinone to ammonium sulfite or bisulfite is from 0.9 to 10.

3. The process according to claim 1, wherein the molar ratio of 2-oxazolidinone to ammonium sulfite or bisulfite is from 1.0 to 2.0.

4. The process according to claim 1, wherein the molar ratio of 2-oxazolidinone to ammonium sulfite or bisulfite is from 1.0 to 1.2.

5. The process according to claim 1, wherein the reaction of 2-oxazolidinone with ammonium sulfite or bisulfite is carried out in a pH range from 5.0 to 9.0.

6. The process according to claim 1, wherein the reaction of 2-oxazolidinone with ammonium sulfite or bisulfite is carried out in a pH range from 6.0 to 8.0.

7. The process according to claim 1, wherein the reaction of 2-oxazolidinone with ammonium sulfite or bisulfite is carried out at a temperature from 60° C. to 160° C.

8. The process according to claim 1, wherein the reaction of 2-oxazolidinone with ammonium sulfite or bisulfite is carried out at a temperature from 90° C. to 120° C.

9. The process according to claim 1, wherein the yield of taurine from 2-oxazolidinone is at least 80%.

* * * * *